United States Patent
Byron et al.

(10) Patent No.: US 9,180,289 B2
(45) Date of Patent: Nov. 10, 2015

(54) ENHANCED LOW FRICTION COATING FOR MEDICAL LEADS AND METHODS OF MAKING

(71) Applicant: Cardiac Pacemakers, Inc., St. Paul, MN (US)

(72) Inventors: Mary M. Byron, Roseville, MN (US); Diana Ma, Roseville, MN (US); James P. Rohl, Prescott, WI (US); Hood Chatham, Scotts Valley, CA (US); Frank De Francesco, Palo Alto, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/963,559

(22) Filed: Aug. 9, 2013

(65) Prior Publication Data

US 2014/0067028 A1   Mar. 6, 2014

Related U.S. Application Data

(60) Provisional application No. 61/694,594, filed on Aug. 29, 2012.

(51) Int. Cl.
| | | |
|---|---|---|
| *A61N 1/05* | (2006.01) | |
| *A61L 27/18* | (2006.01) | |
| *A61L 27/30* | (2006.01) | |
| *A61L 27/50* | (2006.01) | |
| *A61L 31/06* | (2006.01) | |

(Continued)

(52) U.S. Cl.
CPC . *A61N 1/05* (2013.01); *A61L 27/18* (2013.01); *A61L 27/306* (2013.01); *A61L 27/50* (2013.01); *A61L 31/06* (2013.01); *A61L 31/08* (2013.01); *A61L 31/14* (2013.01); *A61L 2400/02* (2013.01); *A61L 2400/10* (2013.01); *A61L 2400/18* (2013.01); *A61L 2420/02* (2013.01)

(58) Field of Classification Search
CPC ......... C08L 83/04; A61F 5/0013; A61N 1/05; A61N 1/00; A61N 1/08
See application file for complete search history.

(56) References Cited

U.S. PATENT DOCUMENTS

| | | |
|---|---|---|
| 3,070,573 A | 12/1962 | Beck |
| 4,131,691 A | 12/1978 | Morley et al. |
| 4,212,719 A | 7/1980 | Osada et al. |

(Continued)

FOREIGN PATENT DOCUMENTS

| | | |
|---|---|---|
| EP | 0124200 B1 | 11/1984 |
| EP | 0585553 A1 | 6/1993 |

(Continued)

OTHER PUBLICATIONS

Glocker, D.A., et al., "Tantalum radiopaque coatings for stents", 2008 Society of Vacuum Coaters, 51st Annual Technical Conference Proceedings, Chicago, IL, Apr. 19-24, 2008, pp. 199-204.

(Continued)

*Primary Examiner* — Deborah Malamud
(74) *Attorney, Agent, or Firm* — Faegre Baker Daniels LLP

(57) ABSTRACT

An implantable or insertable medical device can include a silicone substrate and a plasma-enhanced chemical vapor deposition coating on the silicone substrate. The coating may include a silicon-containing compound. A method of forming the coating is also provided.

4 Claims, 3 Drawing Sheets

(51) Int. Cl.
*A61L 31/14* (2006.01)
*A61L 31/08* (2006.01)

(56) References Cited

U.S. PATENT DOCUMENTS

| | | |
|---|---|---|
| 4,288,426 A | 9/1981 | Stevens |
| 4,521,564 A | 6/1985 | Solomon et al. |
| 4,536,179 A | 8/1985 | Anderson et al. |
| 4,542,752 A | 9/1985 | DeHaan et al. |
| 4,603,704 A | 8/1986 | Mund et al. |
| 4,609,445 A | 9/1986 | Collins |
| 4,632,842 A | 12/1986 | Karwoski et al. |
| 4,656,083 A | 4/1987 | Hoffman et al. |
| 4,687,482 A | 8/1987 | Hanson |
| 4,720,512 A | 1/1988 | Hu et al. |
| 4,946,903 A | 8/1990 | Gardella et al. |
| 4,968,532 A | 11/1990 | Janssen et al. |
| 5,026,607 A | 6/1991 | Kiezulas |
| 5,041,100 A | 8/1991 | Rowland et al. |
| 5,074,313 A | 12/1991 | Dahl et al. |
| 5,077,372 A | 12/1991 | Hu et al. |
| 5,112,457 A | 5/1992 | Marchant |
| 5,133,422 A | 7/1992 | Coury et al. |
| 5,198,033 A | 3/1993 | Kelley et al. |
| 5,277,753 A | 1/1994 | Kelley et al. |
| 5,278,200 A | 1/1994 | Coury et al. |
| 5,364,662 A | 11/1994 | Domenico et al. |
| 5,376,400 A | 12/1994 | Goldberg et al. |
| 5,494,712 A | 2/1996 | Hu et al. |
| 5,593,550 A | 1/1997 | Stewart et al. |
| 5,604,038 A | 2/1997 | Denes et al. |
| 5,620,738 A | 4/1997 | Fan et al. |
| 5,700,559 A | 12/1997 | Sheu et al. |
| 5,702,754 A | 12/1997 | Zhong |
| 5,782,908 A | 7/1998 | Cahalan et al. |
| 5,789,018 A | 8/1998 | Engelson et al. |
| 5,805,264 A | 9/1998 | Janssen et al. |
| 5,811,151 A | 9/1998 | Hendriks et al. |
| 5,849,368 A | 12/1998 | Hostettler et al. |
| 5,866,113 A | 2/1999 | Hendriks et al. |
| 5,914,115 A | 6/1999 | Subramaniam |
| 5,919,570 A | 7/1999 | Hostettler et al. |
| 6,015,597 A | 1/2000 | David |
| 6,049,736 A | 4/2000 | Stewart et al. |
| 6,053,171 A | 4/2000 | Stewart et al. |
| 6,054,188 A | 4/2000 | Tropsha et al. |
| 6,101,973 A | 8/2000 | Stewart et al. |
| 6,129,956 A | 10/2000 | Morra et al. |
| 6,169,127 B1 | 1/2001 | Lohmann et al. |
| 6,180,191 B1 | 1/2001 | Felts |
| 6,197,051 B1 | 3/2001 | Zhong |
| 6,263,249 B1 | 7/2001 | Stewart et al. |
| 6,306,165 B1 | 10/2001 | Patnaik et al. |
| 6,549,811 B2 | 4/2003 | Stewart et al. |
| 6,692,834 B1 | 2/2004 | Martinez et al. |
| 6,713,568 B1 | 3/2004 | Patnaik et al. |
| 7,123,969 B1 | 10/2006 | Chitre |
| 7,217,286 B2 | 5/2007 | Falotico et al. |
| 8,802,603 B2 * | 8/2014 | D'Souza et al. ............ 508/173 |
| 2007/0250142 A1 | 10/2007 | Francis et al. |
| 2008/0280065 A1 | 11/2008 | Fornsel et al. |
| 2011/0022160 A1 | 1/2011 | Flanagan et al. |
| 2012/0123345 A1 | 5/2012 | Felts et al. |
| 2012/0252709 A1 | 10/2012 | Felts et al. |
| 2013/0296988 A1 | 11/2013 | Weber et al. |
| 2014/0142670 A1 | 5/2014 | Radhakrishnan et al. |

FOREIGN PATENT DOCUMENTS

| | | |
|---|---|---|
| EP | 1454651 B1 | 9/2004 |
| GB | 1326197 A | 8/1973 |
| WO | 8909246 A1 | 10/1989 |
| WO | WO03016589 A1 | 2/2003 |
| WO | WO2004103470 A1 | 12/2004 |
| WO | WO2009134901 A1 | 11/2009 |
| WO | WO2010104643 A2 | 9/2010 |
| WO | WO2011031316 A1 | 3/2011 |
| WO | WO2011143329 A2 | 11/2011 |
| WO | WO2011159975 A1 | 12/2011 |

OTHER PUBLICATIONS

International Search Report and Written Opinion issued in PCT/US2013/028692, mailed Sep. 18, 2013, 15 pages.

International Search Report and Written Opinion issued in PCT/US2013/054350, mailed Oct. 23, 2013, 11 pgs.

Karbushev, Valeriy V. et al., "Preparation of Polymer-Nanodiamond Composites with Improved Properties", Advanced Materials Research, vol. 59 (2009), pp. 275-278.

Liang, Xinhua et al., "Novel processing to produce polymer/Ceramic nanocomposites by Atomic Layer Deposition", J. Am Ceram. Soc., vol. 90, No. 1, pp. 57-63, 2007.

Maeng, W.J. et al., "Electrical property improvements of high-k gate oxide by in situ nitrogen incorporation during atomic layer deposition", Applied Physics Letters 90, 062909, 2007, 3 pages.

Partial International Search issued in International Application No. PCT/US2013/028692, mailed Jun. 6, 2013, 3 pages.

Partial International Search Report and Invitation to Pay Additional Fees issued in PCT/US2013/071102 mailed Feb. 17, 2014, 5 pgs.

International Search Report and Written Opinion issued in PCT/US2013/071102, mailed Jun. 18, 2014, 16 pages.

Chan, C.M. et al., "Polymer Surface Modification by Plasmas and Photons", Surface Science Reports 24, 1996, vol. 24, No. 1-2, pp. 1-54.

International Preliminary Examination Report issued in PCT/US2013/071102, completed May 26, 2015, 11 pages.

Komvopoulos, K., "Plasma-Enhanced Surface Modifiction of Low-Linear-Density Polyethylene Catheters", Journal of Mechanics in Medicine and Biology, 2001, vol. 1, No. 1, pp. 17-31.

Marmieri, G. et al., "Evaluation of Slipperiness of Catheter Surfaces", Journal of Biomedical Materials Research, 1996, vol. 33 No. 1 pp. 29-33.

Nagaoka, Shoji et al.,"Low Friction Hydrophilic Surface for Medical Devices", Journal of Bioactive and Compatible Polymers, vol. 5, No. 2, 1990, pp. 212-226.

Nurdin, N. et al., "Reduces Frictional Resistance of Polyurethane Catheter by Means of a Surface Coating Procedure", Journal of Applied Polymer Science, 1996, vol. 61, No. 11, pp. 1939-1948.

Triolo, Philip M. et al., "Surface Modification and Characterization of Some Commonly Used Catheter Materials, II. Friction Characterization", Journal of Biomedical Materials Research, 19883, vol. 17, No. 17 pp. 149-165.

* cited by examiner

ENHANCED LOW FRICTION COATING FOR MEDICAL LEADS AND METHODS OF MAKING

CROSS-REFERENCE TO RELATED APPLICATIONS

This application claims the benefit under 35 U.S.C. section 119(e) to U.S. provisional application No. 61/694,594, entitled "ENHANCED LOW FRICTION COATING FOR MEDICAL LEADS AND METHODS OF MAKING", filed on Aug. 29, 2012, which is herein incorporated by reference in its entirety.

TECHNICAL FIELD

The present invention relates to implantable or insertable medical devices having a reduced coefficient of friction. More specifically, the invention relates to devices having a plasma-enhanced vapor deposited coating and methods of forming the same.

BACKGROUND

Medical electrical leads implanted in or about the heart have been used to reverse certain life-threatening arrhythmias or to stimulate contraction of the heart. For example, the lead may include an electrode connected to a conductor which can apply electrical energy to the heart to return the heart to a normal rhythm. Leads have also been used to sense in the atrium and ventricle of the heart and to deliver pacing pulses to the atrium and ventricle.

The lead may include an outer insulating body for electrically insulating the conductor and allowing only the electrodes to make electrical contact with the body tissue. The outer lead body may be formed from silicone. While silicone is a flexible and biostable material, silicone can form a tacky surface with a high coefficient of friction, which is a drawback, for example, when silicone is used in proximity with moving parts. A high coefficient of friction may also be a drawback during implantation of the lead. In some embodiments, the lead may be implanted by feeding the lead through a catheter system. In these embodiments, it is desirable that the lead is lubricious enough to slide through the catheter system without sticking. Other implantable or insertable medical devices, such as, gastric balloons, bladder devices and breast implants, may include a silicone substrate that would benefit from a low friction surface.

SUMMARY

In Example 1, a method of forming a medical device for insertion or implantation into a patient is provided. The method includes exposing a silicone substrate to plasma in a chamber, and forming a coating on the silicone substrate by plasma-enhanced chemical vapor deposition (PECVD) of a cyclic silicon-containing compound. The PECVD occurs at a chamber pressure of less than about 200 millitorr (mtorr). The coating includes at least about 20 atomic weight percent silicon, of which at least 30 atomic weight percent is in a silica oxidation state.

In Example 2, the method of Example 1, wherein the silicon-containing compound includes octamethyltetracyclosiloxane (OMCTS).

In Example 3, the method of either Example 1 or Example 2, wherein the PECVD occurs at a chamber pressure of about 20 mtorr or less.

In Example 4, the method according to any of Examples 1-3, wherein forming a coating on the silicone substrate includes forming a coating on an inner surface of the silicone substrate In Example 5, an implantable or insertable medical device includes a silicone substrate, and a plasma-enhanced chemical vapor deposited (PECVD) coating on the silicone substrate. The PECVD deposited coating includes a cyclic silicon-containing compound and reduces the coefficient of dynamic friction of the silicone substrate by at least 70%.

In Example 6, the implantable or insertable medical device of Example 5, wherein the coating includes at least about 20 atomic weight percent silicon, of which at least 30 atomic weight percent is in a silica oxidation state.

In Example 7, the implantable or insertable medical device of either Example 5 or Example 6, wherein the silicon-containing compound satisfies the stoichiometry of SiOx, wherein x is from about 1.6 to about 1.8.

In Example 8, the implantable or insertable medical device according to any of Examples 5-7, wherein the cyclic silicon-containing compound includes octamethyltetracyclosiloxane (OMCTS).

In Example 9, the implantable or insertable medical device according to any of Examples 5-8, wherein the coating has a thickness of about 500 nanometers or less.

In Example 10, a method of forming a medical device for insertion or implantation into a patient is provided. The method includes positioning a silicone substrate in a chamber, forming free radicals on at least a portion of a surface of the silicone substrate, and plasma-enhanced chemical vapor depositing (PECVD) a silicon-containing compound onto the silicone substrate at a chamber pressure of less than about 200 millitorr (mtorr) to form a coated substrate.

In Example 11, the method of Example 10, wherein the silicon-containing compound is a cyclic silicon-containing compound.

In Example 12, the method according to Example 10 or Example 11, wherein the silicon-containing compound includes octamethyltetracyclosiloxane (OMCTS).

In Example 13, the method according to any of Examples 10-12, wherein forming free radicals on the silicone substrate includes forming plasma from a gas including at least one member selected from the group consisting of oxygen, argon, tetrafluoromethane ($CF_4$) and nitrogen trifluoride ($NF_3$) and combinations thereof.

In Example 14, the method according to any of Examples 10-13, wherein the PECVD depositing step includes PECVD depositing the silicon-containing compound onto the silicone substrate at a chamber pressure of about 20 mtorr or less.

In Example 15, the method according to any of Examples 10-14, wherein the coated substrate has a coefficient of dynamic friction that is at least about 70% less than that of the silicone substrate.

In Example 16, the method according to any of Examples 10-15, wherein the coated substrate has a coefficient of dynamic friction that is at least about 80% less than that of the silicone substrate.

In Example 17, the method according to any of Examples 10-16, wherein after five temperature cycles between −30° C. and 60° C., the coated silicone substrate has a coefficient of dynamic friction that is at least about 70% less than that of silicone substrate.

In Example 18, the method according to any of Examples 10-17, wherein the PECVD forms a coating having a thickness that is about 50 micrometers or less.

In Example 19, the method according to any of Examples 10-18, wherein the PECVD forms a coating includes at least about 20 atomic weight percent silicon, of which at least about 30 atomic weight percent is in a silica oxidation state.

In Example 20, the method according to any of Examples 10-19, wherein the PECVD forms a conformal coating on an inner surface of the silicone substrate.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
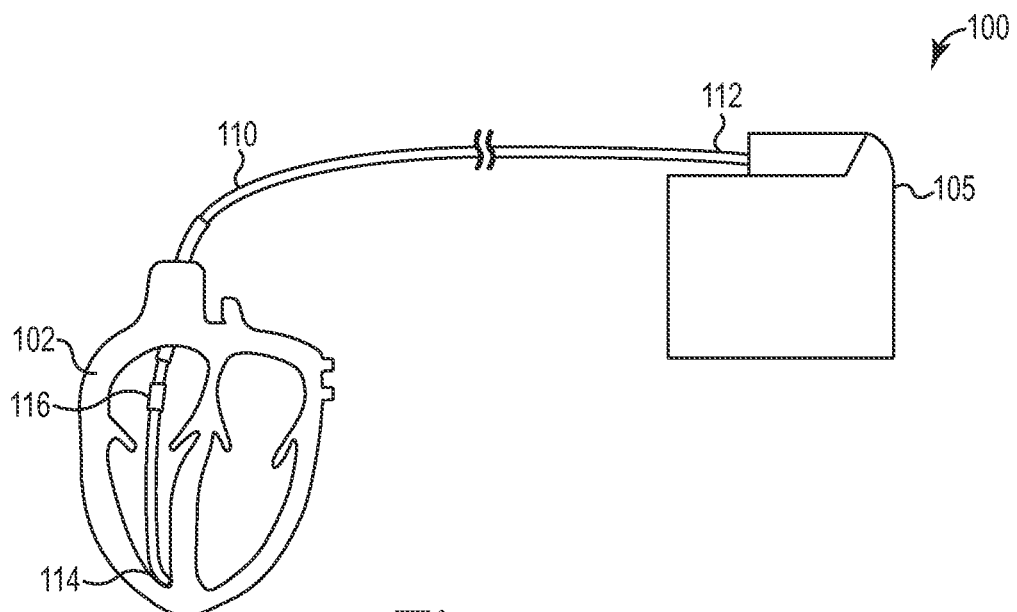
FIG. 1 illustrates an exemplary implantable medical device.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

A more complete understanding of the present invention is available by reference to the following detailed description of numerous aspects and embodiments of the invention. The detailed description of the invention which follows is intended to illustrate but not limit the invention.

An implantable or insertable medical device, such as medical electric devices, gastric balloons, bladder devices and breast implants, may include a silicone substrate. As described herein a coating may be formed on at least a portion of the silicone substrate to provide a surface with a reduced coefficient of both static and dynamic friction. In some embodiments, the coating may completely cover or surround the silicone substrate. The coating may be formed by plasma-enhanced chemical vapor deposition (PECVD). Plasma is a gas in which a significant percentage of the atoms or molecules are ionized. Plasma may be created by radio frequency (RF) or direct current (DC) discharge between two electrodes, and plasma-enhanced chemical vapor deposition may be used to deposit thin films from a gas state (e.g. plasma) on a substrate.

In some embodiments, medical electrical devices can include (a) an electronic signal generating component and (b) one or more leads. The electronic signal generating component commonly contains a source of electrical power (e.g., a battery) and an electronic circuitry package, which produces electrical signals that are sent into the body (e.g., the heart, nervous system, etc.). Leads can include at least one flexible elongated conductive member (e.g., a wire, cable, etc.), which is insulated along at least a portion of its length, generally by an elongated polymeric component often referred to as a lead body. The conductive member is adapted to place the electronic signal generating component of the device in electrical communication with one or more electrodes, which provide for electrical connection with the body of the patient. Leads are thus able to conduct electrical signals to the body of the patient from the electronic signal generating component. Leads may also relay signals from the patient's body to the electronic signal generating component.

Examples of medical electrical devices include, for example, implantable electrical stimulation systems including neurostimulation systems such as spinal cord stimulation (SCS) systems, deep brain stimulation (DBS) systems, peripheral nerve stimulation (PNS) systems, gastric nerve stimulation systems, cochlear implant systems, and retinal implant systems, among others, and cardiac systems including implantable cardiac rhythm management (CRM) systems, implantable cardioverter-defibrillators (ICD's), cardiac resynchronization and defibrillation (CRDT) devices, and subcutaneous implantable cardioverter-defibrillators (SICD's), among others.

FIG. 1 is a schematic illustration of a lead system 100 for delivering and/or receiving electrical pulses or signals to stimulate, shock, and/or sense a heart 102. The lead system 100 includes an optional pulse generator 105 and a medical electrical lead 110. The optional pulse generator 105 includes a source of power as well as an electronic circuitry portion (not shown). In some embodiments, the electronic circuitry can include one or more microprocessors that provide processing and/or evaluation functions, and that can determine and deliver electrical shocks or pulses of different energy levels and timing. The pulse generator 105 can be employed as part of a variety of useful therapies, including for neuro-stimulation or ventricular defibrillation or cardioversion. It can also be used to pace the heart in response to one or more sensed cardiac arrhythmia including fibrillation, cardiac resynchronization, tachycardia, or bradycardia. In some embodiments, the pulse generator 105 can be powered by one or more batteries, though any other internal or external power source may be used for the given application. In some embodiments, the pulse generator 105 can sense intrinsic signals of the heart 102 and generate a series of timed electrical discharges or pulses.

The pulse generator 105 may be generally implanted into a subcutaneous pocket made in the wall of the chest. Alternatively, the pulse generator 105 may be placed in a subcutaneous pocket made in the abdomen, or in another location. It should be noted that while the medical electrical lead 110 is illustrated for use with a heart, the medical electrical lead 110 is suitable for other forms of electrical stimulation/sensing as well.

The medical electrical lead 110 extends from a proximal end 112, where it is coupled with the pulse generator 105 to a distal end 114, where it coupled with a portion of the heart 102, when implanted or otherwise coupled therewith. An outer insulating lead body extends generally from the proximal end 112 to the distal end 114 of the medical electrical lead 110. The outer insulating lead body separates and isolates electrically conductive components within the medical electrical lead 110 from the surrounding tissues of the patient.

Also disposed along at least a portion of the medical electrical lead 110, for example near the distal end 114 of the medical electrical lead 110, is at least one electrode 116. The electrode 116 electrically couples the medical electrical lead 110 with the heart 102 and allows for electrical signals to be delivered from the pulse generator 105 to the target tissue or location. At least one electrical conductor (not shown) is disposed within the lead body and extends generally from the proximal end 112 to the distal end 114 of the medical electrical lead 110. The at least one electrical conductor electrically couples the electrode 116 with the proximal end 112 of the medical electrical lead 110. The electrical conductor carries electrical current and pulses between the pulse generator 105 and the electrode 116, and to and from the heart 102. In one option, the at least one electrical conductor is a coiled conductor. In another option, the at least one electrical conductor includes one or more cables. Typical lengths for such leads vary from about 35 centimeters (cm) to 40 cm to 50 cm to 60 cm to 70 cm to 80 cm to 90 cm to 100 cm to 110 cm to 120 cm, among other values. Typical lead diameters vary from about 12 millimeters (mm) to 15 mm to 18 mm to 21 mm to 24 mm to 27 mm (from about 4 to 5 to 6 to 7 to 8 to 9 French), among other values.

The lead system 100 can include one or more features that enable the medical electrical lead 110 to be secured or fixed within a patient. For example, the medical electrical lead 110 can include passive fixation features, such as one or more tines and/or and active fixation assembly, such as a fixation helix.

Figure 2:
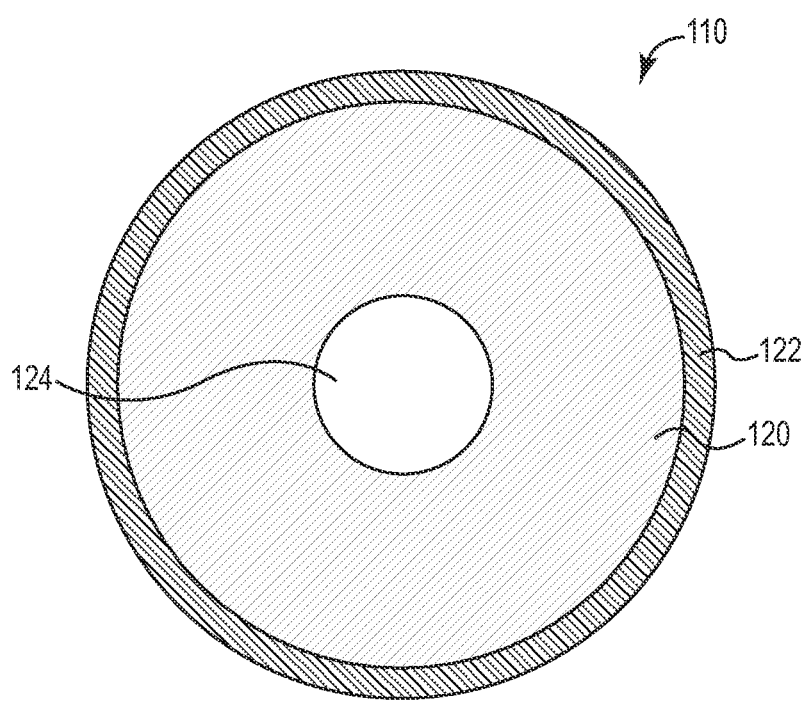
FIG. 2 illustrates an exemplary cross-sectional view of the implantable medical device of FIG. 1.

FIG. 2 is a cross sectional view of an exemplary medical electrical lead 110 which includes a lead body 120, a plasma-enhanced chemical vapor deposited (PECVD) coating 122, and a lumen 124.

The lead body 120 is generally flexible, but substantially non-compressible along its length. The lead body 120 may have any suitable cross-sectional shape. For example, in some embodiments, the lead body 120 may have a substantially circular cross-section. The lead body 120 may be of any suitable size for implantation. In some embodiments, the lead body 120 may have a substantially circular cross-section.

The lead body 120 can include one or more channels or lumens 124 extending axially through the lead body 120 from the proximal end to the distal end of the lead body 120. The lumen 124 forms the inner surface of the lead body 120. The lumen 124 can have any suitable cross-sectional shape, such as substantially circular, rectangular, or triangular cross-sectional shape. The lumen 124 can have a substantially uniform cross-sectional area or the cross-sectional area may vary along the length of the length of the lumen 124 (or the lead body 120).

In some embodiments, lumen 124 may be a conductor lumen and a lead wire may extend through the lumen 124 such that the lead body 120 can isolate the lead wire from the surrounding tissue or environment. Suitable material for the lead body 120 includes silicone and mixtures and composites including silicone. In some embodiments, the composition of the lead body 120 can be substantially uniform along its length. In other embodiments, the composition of the lead body 120 may vary in any direction, including along the length and/or thickness.

The PECVD coating 122 may be disposed on at least a portion of the outer surface of the lead body 120. In some embodiments, the PECVD coating 122 may extend the length of and surround the entire lead body 120 and medical electrical lead 110. For example, the PECVD coating 122 may extend from the proximal end 112 to the distal end 114 of the medical electrical lead 110 and radially surround the entire lead body 120. In other embodiments, the PECVD coating 122 may radially surround the entire or a portion of the lead body 120 and may extend along at least a portion of the length of the lead body 120.

The PECVD coating 122 can be a conformal coating on the outer surface of the lead body 120. That is, the PECVD coating 122 may conform to the topography of the surface of the lead body 120. In some embodiments, the PECVD coating 122 can have a radially and/or axially uniform composition and/or thickness. The lead body 120 may have non-symmetrical or non-uniform features. For example, the lead body 120 may be tapered, have an uneven or variable surface or have other non-uniform features in the axial or radial directions. The conformal properties of the PECVD coating 122 allow the PECVD coating 122 to form a uniform coating (i.e., having a uniform thickness and/or composition) on an uneven or non-uniform substrate.

The PECVD coating 122 can include silicon oxide based chemistry. In some embodiments, suitable silicon oxides may satisfy the stoichiometry $SiO_x$, where x can range from 1.6 to 1.8. The PECVD coating 122 may include silica-like chemistry. For example, in certain embodiments, the PECVD coating 122 can include at least about 20, 21, 22 or 23 atomic weight percent silicon, of which at least about 30, 32, or atomic weight percent is in a silica oxidation state as measured by x-ray photoelectron spectroscopy (XPS) and as determined from the $Si_{2p}$ binding energies. X-ray photoelectron spectroscopy utilizes photoionization and energy-dispersive analysis of emitted photoelectrons to study the composition and electronic state of the surface of a sample. Each element has a characteristic peak in the XPS spectrum at kinetic energies determined by the photon energy and respective binding energies. The presence of peaks at particular energies indicates the presence of particular elements and the intensity of the peaks relates to the concentration of the element. When an element is in different oxidation states, its corresponding energy level will be different. In this way, XPS detects different chemical states or oxidation states of an element as well as the concentration at each state.

The PECVD coating 122 can have a thickness on the micrometer scale. For example, the coating may be less than about 50 micrometers, 25 micrometers or 15 micrometers. Alternatively, the PECVD coating 122 can have a thickness on the nanometer scale. For example, the coating may have a thickness as little as about 10, or 50 nanometers or a thickness as great as about 100, 200 or 500 nanometers or may be within any range delimited by any pair of the foregoing values.

As describe further herein, the PECVD coating 122 may reduce the frictional force experienced when the medical electrical lead 110 is moved within a patient, or upon insertion through a medical system, such as a catheter system. Friction forces include dynamic friction and static friction. Dynamic (or kinetic) friction occurs between two objects that are moving relative to one another, and static friction occurs between two objects that are not moving relative to one another. In some embodiments, the PECVD coating 122 may have a lower coefficient of dynamic friction than the lead body 120. Additionally or alternatively, the PECVD coating 122 may have a lower coefficient of static friction than the lead body 120.

The coefficient of dynamic friction and the coefficient of static friction may be measured with a commercially available friction tester, such as the DL1000 friction tester available from OakRiver. Friction testers are also available from Hanatek and Harland Medical. The coefficient of dynamic friction and the coefficient of static friction of the coated medical electrical lead 110 may be compared to an uncoated medical electrical lead. In certain embodiments, the medical electrical lead 110 including the PECVD coating 122 may have a coefficient of dynamic friction that is at least 70%, 75% or 80% or 85% less than that of a medical electrical lead not including the PECVD coating 122. In further embodiments, the medical electrical lead 110 including the PECVD coating 122 may have a coefficient of static friction that is at least 70%, 75% or 80% or 85% less than that of a medical electrical lead not including the PECVD coating 122. As shown in FIG. 2, the PECVD coating 122 may be formed on the outer surface of the lead body 120, and may increase the lubricity and decrease the coefficient of friction of the outer surface of the lead body 120.

Figure 3:
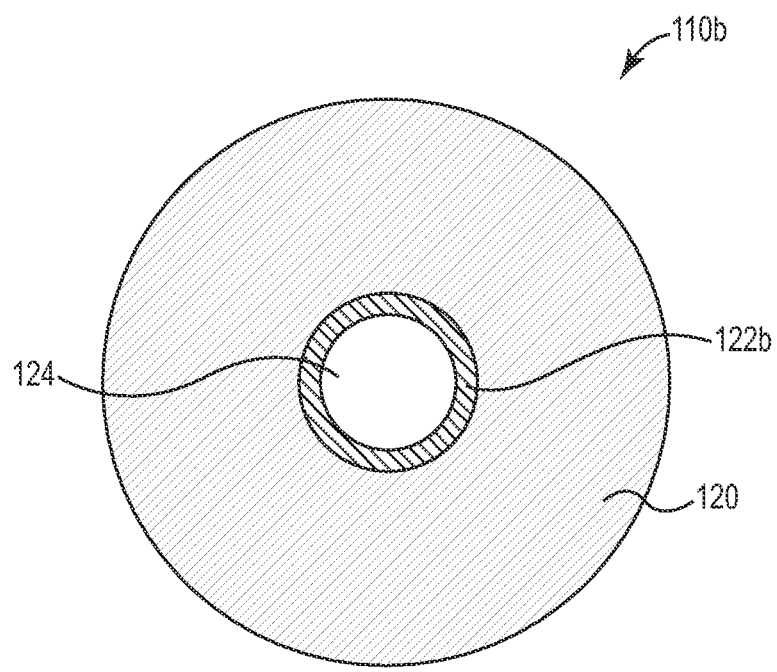
FIG. 3 illustrates an alternative exemplary cross-sectional view of the implantable medical device of FIG. 1.

FIG. 3 is an alternative cross sectional view of the exemplary medical electrical lead 110b in which the PECVD coating 122b is on the inner surface of the lead body 120, adjacent the lumen 124. PECVD coating 122b may improve the lubricity (i.e., reduce the friction coefficient) of the inner surface of the lead body 120. Additionally or alternatively, PECVD coating 122b may reduce wear on the inner surface of the lead body 120 by one or more wires, such as lead wires, extending through the lumen 124.

In some embodiments, PECVD coating 122b has a substantially uniform thickness and/or composition along the length of the lumen 124. The length of the lumen 124 may be up to about one, two or three times the diameter of the lumen 124. Previously, it was difficult to form a coating having a substantially uniform thickness and/or composition along the inner surface of an object. For example, previous deposition methods resulted in a thicker coating along the inner surface near the ends of the object than at the axial center of the object. As described herein, the present method can provide a coating have a substantially uniform thickness along the entire axial length of the inner surface of the lead body 120.

Figure 4:
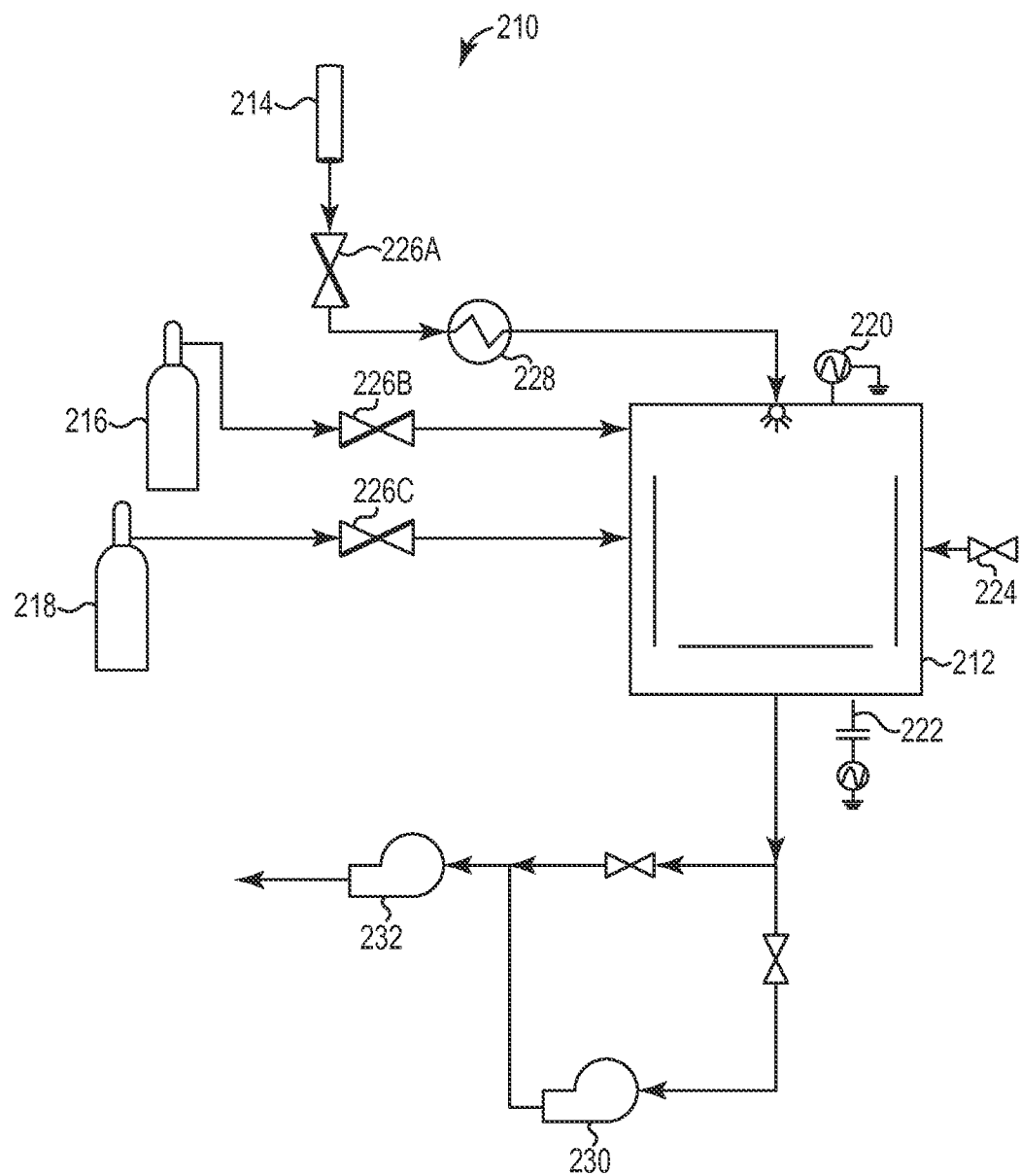
FIG. 4 shows an exemplary system that can be used in relation to embodiments of the present invention.

FIG. 4 is a diagram illustrating an exemplary PECVD system 210, which includes a PECVD chamber 212, a monomer source 214, an oxygen source 216, an argon source 218, a RF power source 220, a RF bias 222, a vent 224, flow control valves 226A, 226B, and 226C, a vaporizer 228, a turbo vacuum pump 230, and a rough vacuum pump 232. The vaporizer 228 is connected between the monomer source 214 and the PECVD chamber 212. The monomer source 214, the oxygen source 216 and the argon source 218 can be fed to the PECVD chamber 212 and the feed flows may be controlled by the flow control valves 226A, 226B and 226C, respectively.

In use, the medical device or a portion of the medical device to be coated is placed in the PECVD chamber 212. The medical device may be masked to control the location of the coating on the medical device. A coating will only form on the surfaces exposed to the environment of the PECVD chamber 212. A coating will not form on the masked portions of the medical device. For example, where the medical device has opening, the opening may be masked to prevent a coating from forming in the openings. In another example where the medical device includes a lumen, the ends of the lumen may be masked such that only the outer surface of the medical device is exposed to the environment of the PECVD chamber 212. In an alternative example, the outer surface of the medical device may be masked such that the inner surface defined by the lumen is exposed to the environment of the PECVD chamber 212 and a coating is formed on the inner surface of the medical device. Suitable masking materials include polytetrafluoroethylene and high density polyethylene, and polyether ether ketone (PEEK).

Once the medical device is positioned in the PECVD chamber 212, the PECVD chamber 212 is purged to remove contaminants from the PECVD chamber 212. Oxygen from the oxygen source 216 is then introduced into the PECVD chamber 212 and plasma is generated using the RF power source 220 and the RF bias 222. More specifically, the plasma is generated by applying an electrical current across the oxygen, which is a dielectric gas. The oxygen plasma may clean or activate the silicone substrate as described herein. Alternatively, the plasma may be generated using argon, tetrafluoromethane ($CF_4$) or nitrogen trifluoride ($NF_3$) gas or combinations thereof in place of or in combination with oxygen.

Following the cleaning or pretreating step, the turbo vacuum pump 230 and the rough vacuum pump 232 are used in conjunction to create an ultralow pressure within the PECVD chamber 212. In some embodiments, the PECVD chamber 212 may have a pressure below 200 millitorr (mtorr). The PECVD chamber 212 may have a pressure as low as 5 mtorr, 10 mtorr, 20 mtorr or 30 mtorr or as high as 40 mtorr, 50 mtorr, 75 mtorr or 100 mtorr or may be within any range delimited by any pair of the foregoing values. In a still further embodiment, the PECVD chamber 212 may have a pressure of about 20 mtorr or about 15 mtorr or less.

After an ultralow pressure has been established within the PECVD chamber 212, the monomer source 214 is introduced and a plasma field is ignited in PECVD chamber 212. The monomer deposits on the substrate to form a coating. In one embodiment, the monomer is a siloxane or silicon-containing compound. Example monomers include linear siloxanes or silicon-containing compounds and cyclic siloxanes or silicon-containing compounds. Suitable linear siloxanes or silicon-containing compounds include hexamethyldisiloxane (HMDSO) and pentamethyl siloxane (PMDSO). Suitable cyclic siloxanes or silicon-containing compounds include octamethyltetracyclosiloxane (OMCTS) and hexamethyl cyclic disiloxane (HMCDS). In some embodiments, the monomer may be a liquid monomer which vaporized by heating prior to introduction into the PECVD chamber 212. For example, the OMCTS monomer may be heated in the vaporizer 228 to about 80° C. prior to introduction into the PECVD chamber 212. Oxygen from the oxygen source 216 may continue to flow to the PECVD chamber 212 during the monomer deposition step to produce the plasma field. In some embodiments, argon, nitrogen, or helium or combinations thereof may be used in place of or in combination with oxygen.

Following deposition of the monomer, the PECVD chamber 212 can be purged with a noble gas, such as argon, or nitrogen, and vented to atmosphere. Purging with the noble gas or nitrogen may prevent contaminants, such as moisture, from entering the PECVD system 210 and contaminating the coating. The coated medical device or portion of the medical device is removed from the PECVD chamber 212. If a portion of a medical device was coated in the PECVD chamber 212, the device can be assembled after removal from the PECVD chamber 212.

The process described herein includes two steps, a cleaning or pretreating step involving plasma in the absence of a monomer and a monomer deposition step involving PECVD of a monomer. The plasma of the cleaning/pretreating step may clean or activate the silicone substrate by forming free radicals on the target surface.

During the monomer deposition step, the monomer reacts with the activated surface and polymerizes to form a coating. As described herein, a siloxane or organic-silicon containing monomer is deposited on the target silicone substrate to form a coating. In one example, the coating is a silicon oxide that satisfies the stoichiometry $SiO_x$, where x is in a range of about 1.6 and about 1.8. The coating may entirely cover or cover at least a portion of the silicone substrate. In one embodiment the coating covers at least a majority the silicone substrate.

As described herein, the coating can be formed by first modifying or activating the silicone substrate with plasma followed by deposition of a siloxane or organic-silicon containing monomer. Not wishing to be bound by theory, it is believed that the monomer covalently bonds to the activated silicone substrate as described herein. In some embodiments, the top layer of the coating may flake or break away if the coating is too thick. For example, the coating may flake if a monomer deposits on another monomer rather than on the silicone substrate. Flaking or breaking away of the coating may not be desired. In certain embodiments, a coating have a thickness less than 50 microns, less than 25 microns or less than 10 microns does not exhibit flaking.

The monomer deposition can occur under ultra low pressure, such as less than 200 mtorr. In some embodiments, the ultra low pressure may result in the monomer forming a silica-containing coating. For example, the ultra low pressure may result in the monomer forming a silica-like coating. As described herein, the coating may be analyzed by XPS and the percentage of silicon elements in the siloxane oxidation state and the silica oxidation state may be determined from the $Si_{2p}$ bond energies. In certain embodiments, a silica-containing coating may include at least 20, 21, 22 or 23 atomic weight percent silicon, of which at least 30, 32 or 35 atomic weight percent is in a silica oxidation state. In some embodiments, silica-containing coating can have improved low-friction properties compared to some siloxane-amorphous coatings. For example, the silica-containing coating may have a lower coefficient of dynamic friction than some siloxane-amorphous coatings.

The current process may be performed as a batch process. In a batch process, a part may be placed in the PECVD chamber 212 prior to the coating process and removed following the coating process. The part is not moved during the coating process. Once a part is positioned in the PECVD chamber 212, the part is not pushed, pulled or otherwise moved until after the coating process is complete and the part is removed from the PECVD chamber 212. Because the coating process described herein does not move the part, the process will not stretch the part or adversely affect any component of the part and/or any dimension of the part. For example, where the part is a lead assembly, which may include a conductor and electrode, the part may be coated in the PECVD chamber 212 without risk of pulling or stretching the conductor (e.g., wires) within the assembly. Alternatively the process may be conducted as a continuous process (also referred to as a reel-to-reel system).

The current batch process may be used to coat overmolded subassemblies. For example the current batch process may be used on fully assembled or partially assembled lead assemblies. In one embodiment, the medical implant can be a portion of a lead assembly including a silicone lead body with an electrode. A conductor may extend through the lumen formed within the silicone lead body. The electrode and the conductor may be masked to prevent deposition of the monomer thereof, and the lead portion may be positioned in the PECVD chamber 212. The coating process described herein may be used to deposit a conformal coating on the unmasked or exposed lead portion. That is, a coating having a uniform thickness and composition can be deposited or formed on the unmasked portion of the silicone lead body. The batch process described herein enables at least a portion of a lead to be assembled prior to the coating process. Additionally, the batch process described herein enables select portions of the lead assembly to be masked to prevent deposition of the coating thereon. For example, the ends of a lead assembly may be masked to prevent deposition of the monomer on the inner surface of the assembly, including the conductor within the assembly.

Medical devices may be subject to sterilization and temperature cycling. In certain embodiments, the coating is not significantly affected by sterilization processes or temperature cycling. In some embodiments, the medical device can be sterilized by exposure to ethylene oxide. The medical device may also be subjected to temperature cycles between −30° C. and 60° C., with a minimum dwell time of one hour at each extreme. In some embodiments, five temperature cycles may be performed. That is, the medical device may be subjected to −30° C. for a minimum of one hour, the temperature can then be increased to 60° C. and the medical device can be subjected to this temperature for at least one hour to complete one temperature cycle. This process can be repeated up to four additional times, for a total of five temperature cycles, for example. The sterilization and temperature cycling may affect the lubricity and coefficients of friction of the coated substrate. In some embodiments, the coated substrate has an improved lubricity, coefficient of dynamic friction and/or coefficient of static friction as compared to an uncoated substrate. In some embodiments, after at least three sterilization processes and three temperature cycles, the coated substrate may have a reduced coefficient of dynamic friction and/or static friction as compared to the substrate without the coating. For example, after at least three sterilization processes and three temperature cycles, the coated substrate may have a coefficient of dynamic friction and/or coefficient of static friction that is reduced by at least 40%, at least 50%, or at least 60% as compared to coefficient of friction of the substrate without the coating.

Experimental Section

Coating Composition—Samples 1-3

Samples 1-3 compared silicone tubing having the PECVD coating disclosed herein to silicone tubing having a commercially available silicon coating and uncoated silicone tubing. The samples were compared before and after a sterilization and temperature cycling process to determine the effects of heat on the coatings.

Sample 1 was a silicone tubing having a PECVD coating as described herein on the outer surface. The coating was formed by PECVD of OMCTS using oxygen plasma at 10-15 mtorr. The coating a thickness was from about 90 to about 100 nanometers.

Sample 2 was a silicone tubing having a commercially available silicone coating. The coating was formed by applying a commercially available siloxane containing coating on the outer surface of a silicone tubing.

Sample 3 was an uncoated silicone tubing.

Samples 1 and 2 were exposed to ethylene oxide for sterilization. After sterilization, Samples 1 and 2 were subjected to five temperature cycles between −30° C. and 60° C., with a minimum dwell time of one hour at each extreme. The samples after sterilization and temperature cycling are identified as Sample 1S and Sample 2S.

The atomic composition of carbon, nitrogen, oxygen and silicon at the surface of each sample was analyzed by X-ray photoelectron spectroscopy (XPS) using the conditions of Table A.

TABLE A

| | |
|---|---|
| Instrument | PHI Quantum 2000 |
| X-ray source | Monochromated $Alk_\alpha$ 1486.6 eV |
| Take-off angle | ~45° |
| Analysis area | ~200 μm |
| Charge Correction | C—C/C—H/C—Si in C1s to 284.8 eV |
| Charge Neutralization | Low energy electron and ion floods |

The results in atomic weight percent are shown in Table 1. The values are normalized to 100% of the elements detected. XPS does not detect hydrogen or helium.

TABLE 1

|          | C    | N   | O    | Si   |
|----------|------|-----|------|------|
| Sample 1 | 39.8 | 0.0 | 35.3 | 24.8 |
| Sample 2 | 47.4 | 0.0 | 29.0 | 23.7 |
| Sample 3 | 49.4 | 0.6 | 28.6 | 21.4 |
| Sample 1S| 40.8 | 0.8 | 34.6 | 23.8 |
| Sample 2S| 48.1 | 0.4 | 29.2 | 22.2 |

The atomic compositions of Samples 1 and 2 before and after sterilization did not significantly differ indicating that the coatings of Samples 1 and 2 are stable under the sterilization conditions.

The silicon oxidation states of the samples were also determined by XPS and the results are in Table 2. The values in Table 2 are percentages of the total atomic concentration of the silicone content shown in Table 1.

TABLE 2

|          | Silicone/siloxane (atomic weight percent) | Silica (atomic weight percent) |
|----------|-------------------------------------------|--------------------------------|
| Sample 1 | 59 | 41 |
| Sample 2 | 78 | 22 |
| Sample 3 | 88 | 12 |
| Sample 1S| 61 | 39 |
| Sample 2S| 77 | 23 |

Table 2 demonstrates that Sample 1 (one embodiment of the PECVD coating described herein) contained a greater amount of silica.

Coefficient of Friction—Samples 4-6

Samples 4, 5 and 6 compare the static coefficient of friction (COFs) and the dynamic coefficient of friction (COFd) of silicone substrates having a PECVD coating (Samples 5 and 6) on the outer surface as described herein to uncoated silicone tubing (Sample 4).

The samples were tested using a Oak River DL1000 friction tester. A sample size of ⅝ inch width by 4.5 inch length was used. The friction test was performed at 100 grams force grip and 3 mm per second under dry conditions. The samples were run in triplicate and the average for each sample was calculated.

TABLE 3

|          |                      | Average COFs | Average COFd | % decrease over Sample 4 COFs | COFd |
|----------|----------------------|--------------|--------------|-------------------------------|------|
| Sample 4 | Uncoated silicone    | 7.12         | 8.27         | —                             | —    |
| Sample 5 | PECVD coated silicone| 2.11         | 2.10         | 70%                           | 75%  |
| Sample 6 | PECVD coated silicone| 1.05         | 1.28         | 85%                           | 74%  |

As shown in Table 3, the PECVD coating reduced the static coefficient of friction and the dynamic coefficient of friction as compared to an uncoated substrate.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An implantable or insertable medical device comprising:
   a silicone substrate; and
   a plasma-enhanced chemical vapor deposition (PECVD) deposited coating comprising a cyclic silicon-containing compound on the silicone substrate, wherein the coating includes at least about 20 atomic weight percent silicon, of which at least 30 atomic weight percent is in a silica oxidation state, wherein the coating reduces a coefficient of friction of the silicone substrate by at least 70%.

2. The implantable or insertable medical device of claim 1, wherein the silicon-containing compound satisfies the stoichiometry of SiOx, wherein x is from about 1.6 to about 1.8.

3. The implantable or insertable medical device of claim 1, wherein the cyclic silicon-containing compound comprises octamethyltetracyclosiloxane (OMCTS).

4. The implantable or insertable medical device of claim 1, wherein the coating has a thickness of about 500 nanometers or less.

* * * * *